United States Patent [19]

Takahashi et al.

[11] Patent Number: 4,670,489

[45] Date of Patent: Jun. 2, 1987

[54] PIPERIDINE DERIVATIVES, THEIR PRODUCTION AND USE AS STABILIZERS

[75] Inventors: Yukoh Takahashi; Tatsuo Kaneoya, both of Toyonaka; Eizo Okino, Kurashiki; Yuzo Maegawa, Toyono; Haruki Okamura, Osaka; Shinichi Yachigo, Toyonaka; Tamaki Ishii, Suita, all of Japan

[73] Assignee: Sumitomo Chemical Company, Ltd., Osaka, Japan

[21] Appl. No.: 805,298

[22] Filed: Dec. 5, 1985

[30] Foreign Application Priority Data

Dec. 11, 1984 [JP] Japan ................... 59-261198

[51] Int. Cl.⁴ ................... C07K 5/34; C07D 401/12
[52] U.S. Cl. ................... 524/103; 524/99; 524/102; 546/188; 546/216; 546/223
[58] Field of Search ............ 546/188, 216, 223; 524/99, 102, 103

[56] References Cited

U.S. PATENT DOCUMENTS 4,578,472  3/1986  Yoshimura et al. ............ 546/188

Primary Examiner—Robert T. Bond

[57] ABSTRACT

The present invention relates to a piperidine derivative represented by the general formula (I),

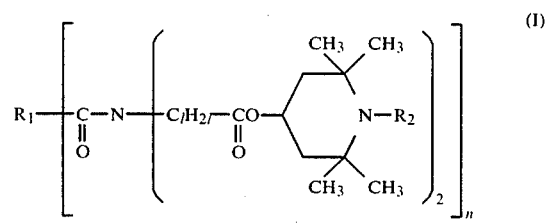

wherein $R_1$ is a uni- or divalent carboxylic acid residue, $R_2$ is a hydrogen atom or a $C_1$-$C_3$ alkyl or $C_1$-$C_{18}$ acyl group, $l$ is an integer of 1 to 3 and $n$ is 1 or 2, its production and a stabilizer for organic substances containing it as an effective ingredient.

22 Claims, No Drawings

PIPERIDINE DERIVATIVES, THEIR PRODUCTION AND USE AS STABILIZERS

The present invention relates to a piperidine derivative represented by the general formula (I),

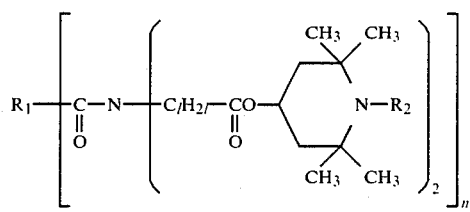

wherein $R_1$ is a uni- or divalent carboxylic acid residue, $R_2$ is a hydrogen atom or a $C_1-C_3$ alkyl or $C_1-C_{18}$ acyl group, l is an integer of 1 to 3 and n is 1 or 2, its production and a stabilizer for organic substances containing it an an effective ingredient.

It is well known that synthetic resins such as polyethylene, polypropylene, polyvinyl chloride, polyurethane, ABS resin, etc. and organic substances such as paints deteriorate in quality by the action of light, thereby showing a remarkable reduction in the physical property accompanied by phenomena such as softening, embrittlement, discoloration and the like.

For the purpose of preventing such deterioration by light, it is so far known to use various kinds of light stabilizer such as 2-hydroxy-4-methoxybenzophenone, 2-hydroxy-4-n-octoxybenzophenone, 2-(2-hydroxy-5-methylphenyl)benzotriazole, 2-(2-hydroxy-3-tert-butyl-5-methylphenyl)-5-chlorobenzotriazole, 2-(2-hydroxy-3,5-dipentylphenyl)benzotriazole, ethyl 2-cyano-3,3-diphenylacrylate, 2,4-di-tert-butylphenyl 3,5-di-tert-butyl-4-hydroxybenzoate, [2,2'-thiobis(4-tert-octylphenolate)]-n-butylamine.nickel(II), Ni salt of bis(3,5-di-tert-butyl-4-hydroxybenzylphosphoric acid monoethyl ester), bis(2,2,6,6-tetramethyl-4-piperidyl)sebacate and the like. These light stabilizers, however, are not yet quite satisfactory in terms of light fastness.

The present inventors extensively studied to solve these problems, and as a result, found that the piperidine derivative represented by the foregoing general formula (I) has excellent effect in preventing organic substances such as synthetic resins, paints, etc. from deterioration by light. The present inventors thus attained to the present invention.

The present inventors were the first to synthesize said piperidine derivative of the present invention, and it can be produced by:

(1) reacting an iminodialkanoic acid derivative represented by the general formula (II),

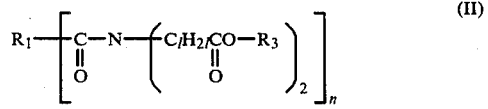

wherein $R_1$, l and n have the same meanings as described above, and $R_3$ is a $C_1-C_4$ alkyl group, with a piperidinol derivative represented by the general formula (III),

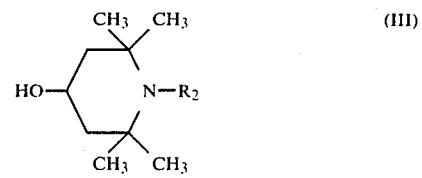

wherein $R_2$ has the same meaning as described above, or (2) reacting an iminodialkanoic acid derivative represented by the general formula (IV),

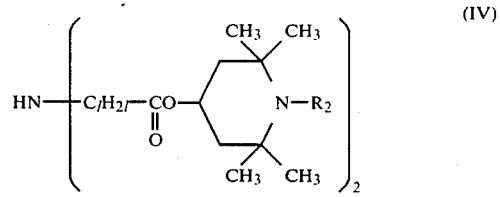

wherein $R_2$ and l have the same meanings as described above,
with a carboxylic acid halide represented by the general formula (V),

wherein $R_1$ and n have the same meanings as described above, and X is a halogen atom.

The uni- or divalent carboxylic acid residue represented by $R_1$ includes the following groups (a) to (i):

(a) A univalent carboxylic acid residue wherein the carboxylic acid residue is a $C_1-C_{20}$ non-cycloaliphatic group Specifically, there are given the residues of acetic acid, propionic acid, butyric acid, isobutyric acid, valeric acid, caproic acid, caprylic acid, capric acid, lauric acid, palmitic acid, stearic acid, etc.

(b) A univalent carboxylic acid residue having a cycloaliphatic group linked to the end of the carboxylic acid residue shown in (a)

(c) A univalent carboxylic acid residue having an aromatic group linked to the end of the carboxylic acid residue shown in (a)

(d) A divalent carboxylic acid residue wherein the carboxylic acid residue is a $C_1-C_{18}$ non-cycloaliphatic group Specifically, there are given the residues of malonic acid, maleic acid, succinic acid, glutaric acid, adipic acid, pimelic acid, suberic acid, azelaic acid, sebacic acid, tetradecane-1,14-dicarboxylic acid, octadecane-1,18-dicarboxylic acid, 6-ethyldodecane-1,12-dicarboxylic acid, 7-ethylhexadecane-1,16-dicarboxylic acid, etc.

(e) A divalent carboxylic acid residue wherein the carboxylic acid residue is a single bond Specifically, there is given an oxalic acid residue.

(f) A divalent carboxylic acid residue wherein the carboxylic acid residue is a $C_5-C_{16}$ cycloaliphatic group Specifically, there are given the residues of 1,2-cyclopentanedicarboxylic acid, 1,1-cyclopentanediacetic acid, 1,2-cyclohexanedicarboxylic acid, 1,4-cyclohexanedicarboxylic acid, 1,1-cyclohexanediacetic acid, 1,1-cyclotridecanediacetic acid, 5-norbornane-2,3-dicarboxylic acid, etc.

(g) A divalent carboxylic acid residue wherein the carboxylic acid residue is an aromatic group having 6 or 10 carbon atoms Specifically, there are given the residues of phthalic acid, isophthalic acid, terephthalic acid, 1,4-naphthalenedicarboxylic acid, 1,8-naphthalenedicarboxylic acid, etc.

(h) A divalent carboxylic acid residue wherein the carboxylic acid residue is an aliphatic group having an aromatic group linked to the side or main chain, the aliphatic moiety having 1 to 16 carbon atoms Specifically, there are given the residues of phenylmalonic acid, o-phenylenediacetic acid, m-phenylenediacetic acid, p-phenylenediacetic acid, 7,8-diphenyltetradecane-1,14-dicarboxylic acid, etc.

(i) A $C_4$–$C_{20}$ divalent carboxylic acid residue having hetero-atoms such as nitrogen, sulfur, etc. in the carboxylic acid residue.

Examples of $R_2$ include hydrogen, alkyl groups such as methyl, ethyl, isopropyl, etc. and acyl groups such as acetyl, propionyl, valeryl, palmitoyl, stearoyl, oleoyl, etc. Examples of $R_3$ include alkyl groups such as methyl, ethyl, n-propyl, n-butyl, isobutyl, etc. Specific examples of —$C_lH_{2l}$— include a methylene, ethylene, isopropylene and trimethylene groups, etc.

The reaction (1) may be carried out with or without a solvent. The solvent which may be used includes aromatic hydrocarbons (e.g. toluene, xylene), aliphatic hydrocarbons (e.g. n-hexane, n-heptane), alicyclic hydrocarbons (e.g. cyclohexane), water-soluble polar solvents (e.g. N,N-dimethylformamide, dimethyl sulfoxide, sulfolane), ethers (e.g. diethyl ether, THF, dioxane, methyl cellosolve) and alcohols (e.g. methanol).

This reaction is ester-interchange reaction, and it can normally be promoted with a basic catalyst. This basic catalyst includes metal hydroxides (e.g. sodium hydroxide, potassium hydroxide, lithium hydroxide), hydrides (e.g. sodium borohydride, sodium hydride, lithium hydride), metal amides (e.g. sodium amide, lithium amide), alkali metal alkoxides and alkali metal phenoxides (e.g. potassium tert-butoxide, sodium methoxide, sodium phenoxide) and the like. Preferred catalysts among them are potassium tert-butoxide, lithium amide and sodium hydroxide. The amount of the catalyst used is in the range of 0.01 to 3 times by mole, preferably 0.1 to 1 time by mole based on 1 mole of the piperidinol derivative, a starting material, represented by the general formula (II).

The reaction temperature is in the range of 0° to 200° C., preferably 30° to 160° C.

In the reaction (1), the molar ratio of the piperidinol derivative represented by the general formula (III) to the iminodialkanoic acid derivative represented by the general formula (II) is in the range of 2:1 to 5:1 when n is 1, and 4:1 to 10:1 when n is 2. The amount of the solvent used is not particularly limited, but generally, it is in the range of 0 to 20 times by weight based on the iminodialkanoic acid derivative of the general formula (III).

After completion of the reaction, the catalyst used is removed by filtration, washing with water or the like, after which the solvent is removed by evaporation to obtain the product.

The reaction (2) is carried out in an inert solvent in the presence of a dehydrohalogenating agent.

The inert solvent includes aliphatic hydrocarbons (e.g. n-hexane, n-heptane), alicyclic hydrocarbons (e.g. cyclohexane), aromatic hydrocarbons (e.g. toluene, xylene), water-soluble polar solvents (e.g. N,N-dimethylformamide, dimethyl sulfoxide, sulfolane), ethers (e.g. diethyl ether, dioxane, THF), halogenated hydrocarbons (e.g. dichloromethane, chloroform), esters (e.g. ethyl acetate, butyl acetate) and the like. These solvents may be used alone or in combination.

The dehydrohalogenating agent includes tertiary amines (e.g. triethylamine, dimethylaniline, N,N-dimethylbenzylamine, tetramethylurea), pyridine derivatives [e.g. pyridine, 4-(N,N-dimethylamino)pyridine], carbonates (e.g. sodium carbonate, potassium hydrogencarbonate) and the like. In place of the dehydrohalogenating agents given above, to use the iminodialkanoic acid derivative itself represented by the general formula (IV) is also quite permissible. The amount of the dehydrohalogenating agent used is in the range of 0.9 to 1.2 equivalents based on 1 equivalent of the carboxylic acid halide.

The halogen atom of the carboxylic acid halide includes chlorine, bromine and iodine, of which chlorine is most preferred, bromine being the next one. This carboxylic acid halide is synthesized from the corresponding carboxylic acid by the well-known method.

The molar ratio of the iminodialkanoic acid derivative of the general formula (IV) to the uni- or divalent carboxylic acid halide of the general formula (V) is in the range of 0.9:1 to 1.1:1 for the univalent carboxylic acid halide, and 1.8:1 to 2.2:1 for the divalent one.

The reaction temperature is in the range of $-30°$ to 120° C., preferably $-10°$ to 80° C.

The amount of the solvent used is not particularly limited, but generally, it is in the range of 1 to 30 times by weight based on the iminodialkanoic acid derivative of the general formula (IV).

After completion of the reaction, the salt of the dehydrohalogenating agent with hydrogen halide formed during the reaction is removed by filtration, washing with water or the like, after which the solvent is removed by evaporation to obtain the product.

The piperidine derivative of the general formula (I) obtained by the foregoing methods (1) and (2) can be purified by the well-known methods such as recrystallization, washing with solvents, separation by chromatography, etc.

Typical examples of the piperidine derivative of the present invention thus obtained include the followings:

N,N-bis(2,2,6,6-tetramethyl-4-piperidinyloxycarbonylmethyl)acetamide

N,N-bis(2,2,6,6-tetramethyl-4-piperidinyloxycarbonylmethyl)octanecarboxylic acid amide N,N-bis(2,2,6,6-tetramethyl-4-piperidinyloxycarbonylmethyl)octadecanecarboxylic acid amide N,N-bis(1,2,2,6,6-pentamethyl-4-piperidinyloxycarbonylmethyl)dodecanecarboxylic acid amide N,N-bis(2,2,6,6-tetramethyl-4-piperidinyloxycarbonylmethyl)cyclohexanepropionamide N,N-bis(2,2,6,6-tetramethyl-4-piperidinyloxycarbonylmethyl)cyclohexanecarboxylic acid amide N,N-bis(1,2,2,6,6-pentamethyl-4-piperidinyloxycarbonylmethyl)cyclohexanepropionamide N,N-bis(2,2,6,6-tetramethyl-4-piperidinyloxycarbonylmethyl)phenylpropionamide N,N-bis(1,2,2,6,6-pentamethyl-4-piperidinyloxycarbonylmethyl)-3-tertbutyl-5-methyl-4-hydroxyphenylpropionamide N,N-bis(1,2,2,6,6-pentamethyl-4-piperidinyloxycar-
bonylmethyl)benzamide N,N,N',N'-tetrakis(2,2,6,6-tetramethyl-4-piperidinylox-
ycarbonylmethyl)malonamide N,N,N',N'-tetrakis(2,2,6,6-tetramethyl-4-piperidinylox-
ycarbonylmethyl)adipoylamide N,N,N',N'-tetrakis(2,2,6,6-tetramethyl-4-piperidinylox-
ycarbonylmethyl)sebacoylamide N,N,N',N'-tetrakis(2,2,6,6-tetramethyl-4-piperidinylox-
ycarbonylmethyl)tetradecanedicarboxylic acid amide N,N,N',N'-tetrakis(1,2,2,6,6-pentamethyl-4-
piperidiinyloxycarbonylmethyl)-7-ethylhexadecane-
1,12-dicarboxylic acid amide N,N,N',N'-tetrakis(2,2,6,6-tetramethyl-4-piperidinylox-
ycarbonylmethyl)oxamide N,N,N',N'-tetrakis(2,2,6,6-tetramethyl-4-piperidinylox-
ycarbonylmethyl)-1,4-cyclohexanedicarboxylic acid
amide N,N,N',N'-tetrakis(2,2,6,6-tetramethyl-4-piperidinylox-
ycarbonylmethyl)-5-norbornane-2,3-dicarboxylic
acid amide N,N,N',N'-tetrakis(2,2,6,6-tetramethyl-4-piperidinylox-
ycarbonylmethyl)phthalamide N,N,N',N'-tetrakis(2,2,6,6-tetramethyl-4-piperidinylox-
ycarbonylmethyl)-1,4-naphthalenedicarboxylic acid
amide N,N,N',N'-tetrakis(1,2,2,6,6-pentamethyl-4-
piperidinyloxycarbonylmethyl)isophthalamide N,N,N',N'-tetrakis(1,2,2,6,6-pentamethyl-4-
piperidinyloxycarbonylmethyl)phenylmalonamide N,N,N',N'-tetrakis(1,2,2,6,6-pentamethyl-4-
piperidinyloxycarbonylmethyl)-7,8-diphenyltetra-
decane-1,14-dicarboxylic acid amide N,N,N',N'-tetrakis(2,2,6,6-tetramethyl-4-piperidinylox-
ycarbonylmethyl)thiodipropionamide N,N,N',N'-tetrakis(1,2,2,6,6-pentamethyl-4-
piperidinyloxycarbonylmethyl)iminodiacetamide When the piperidine derivative of the present invention is used as a stabilizer for synthetic resins and paints, its amount blended with the synthetic resins or paints is generally 0.01 to 5 parts by weight, preferably 0.05 to 2 parts by weight based on 100 parts by weight of the synthetic resins. For blending the both, the well-known apparatus and methods for incorporating stabilizers, pigments, fillers, etc. in synthetic resins may be used almost as such.

In using the stabilizer for synthetic resin of the present invention, other additives such as antioxidants, light stabilizers, metal deactivators, metal soaps, nucleating agents, lubricants, antistatic agents, flame retardants, pigments, fillers and the like may be used together.

Particularly, the thermal stability and oxidation stability of organic substances such as synthetic resins and paints can be improved by using a phenolic type antioxidant together. Such antioxidant includes for example 2,6-di-tert-butyl-4-methylphenol, n-octadecyl β-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris(3,5-di-tert-butyl-4-hydroxybenzyl)-benzene, 1,3,5-tris(3,5-di-tert-butyl-4-hydroxybenzyl)isocyanulate, 1,3,5-tris[β-(3,5-di-tert-butyl-4-hydroxyphenyl)propionyloxyethyl]isocyanulate, 1,3,5-tris(2,6-dimethyl-3-hydroxy-4-tert-butylbenzyl)isocyanulate, pentaerythritol tetrakis[β-(3,5-di-tert-butyl-4-hydroxyphenyl)propionate] and the like.

Also, the color of the organic substances can be improved by using a phosphite type antioxidant together. Such antioxidant includes for example tris(nonylphenyl)phosphite, distearyl pentaerythritol diphosphite, tris(2,4-di-tert-butylphenyl)phosphite, tris(2-tert-butyl-4-methylphenyl)phosphite, bis(2,4-di-tert-butylphenyl)-pentaerythritol diphosphite, tetrakis(2,4-di-tert-butyl-phenyl) 4,4'-diphenylene diphosphonite and the like.

Further, a sulfur-containing antioxidant may be used together. Such antioxidant includes for example dilauryl thiodipropionate, dimyristyl thiodipropionate, distearyl thiodipropionate, pentaerythritol tetrakis(β-laurylthiopropionate), pentaerythritol tetrakis(β-hexylthiopropionate) and the like.

Synthetic resins stabilized by the stabilizer for organic substance of the present invention includes for example low-density polyethylene, high-density polyethylene, linear low-density polyethylene, chlorinated polyethylene, EVA resin, polypropylene, polyvinyl chloride, methacrylic resin, polystyrene, impact-resistant polystyrene, ABS resin, AES resin, MBS resin, polyethylene terephthalate, polybutylene terephthalate, polyamide, polyimide, polycarbonate, polyacetal, polyurethane, unsaturated polyester resin and the like. Paints stabilized by said stabilizer includes for example oil paints, spirit paints, cellulose derivative paints, synthetic resin paints, synthetic resin emulsion paints, water-based baking paints and the like.

The present invention will be illustrated in detail with reference to the following examples, but it is not limited to these examples.

EXAMPLE 1

N,N-bis(2,2,6,6-tetramethyl-4-piperidinyloxycarbonylmethyl)octanecarboxylic acid amide (HA-1)

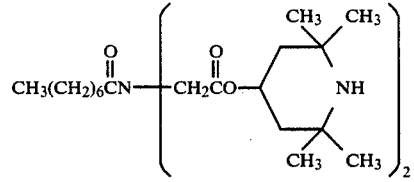

To a 300-ml flask equipped with a thermometer, a stirrer and a distilling apparatus were added 25.2 g (0.08 mole) of N,N-bis(ethoxycarbonylmethyl)octanecarboxylic acid amide, 27.0 g (0.17 mole) of 2,2,6,6-tetramethyl-4-piperidinol, 50 ml of toluene and 0.5 g (0.04 mole) of potassium tert-butoxide, and after the temperature was raised to 110° C., reaction was carried out at 110° to 130° C. for 8 hours, during which the solvent was distilled.

After completion of the reaction, the reaction mixture was cooled to room temperature and dissolved in 100 ml of toluene. The catalyst was removed by filtration, and toluene in the filtrate was distilled to obtain 38.4 g of a residue (yield, 89.3%). The residue was dissolved in hexane, treated with activated charcoal and recrystallized to obtain 32.3 g of N,N-bis(2,2,6,6-tetramethyl-4-piperidinyloxycarbonylmethyl)octanecarboxylic acid amide as a white crystal (yield, 75%). Melting point, 78°–79° C.

A parent ion peak (537) was confirmed by FD-MS.

| Elementary analysis (for $C_{30}H_{55}N_3O_5$): | | | |
|---|---|---|---|
| | C (%) | H (%) | N (%) |
| Found | 67.01 | 10.43 | 7.77 |

-continued

Elementary analysis (for $C_{30}H_{55}N_3O_5$):

| | C (%) | H (%) | N (%) |
|---|---|---|---|
| Calculated | 67.00 | 10.31 | 7.81 |

EXAMPLE 2

N,N-bis(2,2,6,6-tetramethyl-4-piperidinyloxycarbonylmethyl)butanecarboxylic acid amide (HA-2)

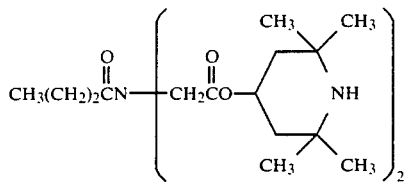

To the same reactor as in Example 1 were added 23.3 g (0.09 mole) of N,N-bis(ethoxycarbonylmethyl)-butanecarboxylic acid amide, 28.2 g (0.18 mole) of 2,2,6,6-tetramethyl-4-piperidinol, 50 ml of toluene and 0.5 g (0.04 mole) of potassium tert-butoxide. Reaction and after-treatment were carried out in the same manner as in Example 1 to obtain 30.3 g of N,N-bis(2,2,6,6-tetramethyl-4-piperidinyloxycarbonylmethyl)-butanecarboxylic acid amide as a white crystal (yield, 70%). Melting point, 96°-98° C.

A parent ion peak (481) was confirmed by FD-MS.

Elementary analysis (for $C_{26}H_{47}N_3O_5$):

| | C (%) | H (%) | N (%) |
|---|---|---|---|
| Found | 64.55 | 9.76 | 8.54 |
| Calculated | 64.83 | 9.84 | 8.72 |

EXAMPLE 3

N,N,N',N'-tetrakis(2,2,6,6-tetramethyl-4-piperidinyloxycarbonylmethyl)adipoylamide (HA-3)

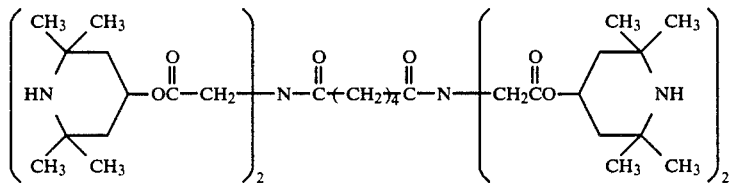

To the same reactor as in Example 1 were added 8.0 g (0.016 mole) of N,N,N',N'-tetrakis(ethoxycarbonylmethyl)adipoylamide, 10.4 g (0.066 mole) of 2,2,6,6-tetramethyl-4-piperidinol, 70 ml of toluene and 0.5 g (0.04 mole) of potassium tert-butoxide, and reaction was carried out in the same manner as in Example 1.

After completion of the reaction, the reaction mixture was dissolved in 200 ml of toluene. Crystals deposited as precipitate by repeating washing with water and phase separation. The crystal was collected by filtration to obtain 9.4 g of N,N,N',N'-tetrakis(2,2,6,6-tetramethyl-4piperidinyloxycarbonylmethyl)adipoylamide as a white crystal (yield, 63%). Melting point, 133°-134° C.

A parent ion peak (932) was confirmed by FD-MS.

Elementary analysis (for $C_{50}H_{88}N_6O_{10} \cdot 2H_2O$):

| | C (%) | H (%) | N (%) |
|---|---|---|---|
| Found | 62.05 | 9.48 | 8.66 |
| Calculated | 61.96 | 9.57 | 8.67 |

EXAMPLE 4

N,N,N',N'-tetrakis(2,2,6,6-tetramethyl-4-piperidinyloxycarbonylmethyl)terephthalamide (HA-4)

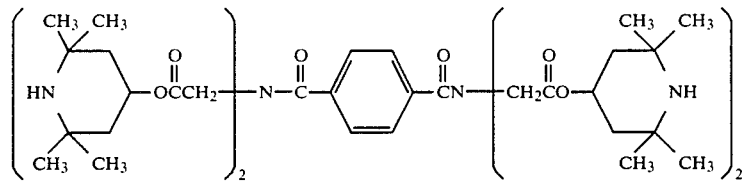

To the same reactor as in Example 1 were added 19.8 g (0.039 mole) of N,N,N',N'-tetrakis(ethoxycarbonylmethyl)terephthalamide, 29.2 g (0.186 mole) of 2,2,6,6-tetramethyl-4-piperidinol, 100 g of n-octane and 0.4 g (0.017 mole) of lithium amide, and after the temperature was raised to 125° C., reaction was carried out at 125° to 135° C. for 3 hours, during which the solvent was distilled.

After completion of the reaction, the reaction mixture was cooled to room temperature. Crystals deposited as precipitate after washing with water and phase separation. The crystal was collected by filtration to obtain 28.3 g of N,N,N',N'-tetrakis(2,2,6,6-tetramethyl-4-piperidinyloxycarbonylmethyl)terephthalamide as a white crystal (yield, 76%). Melting point, 191°-193° C.

A parent ion peak (952) was confirmed by FD-MS.

Elementary analysis (for $C_{52}H_{84}N_6O_{10} \cdot 2H_2O$):

| | C (%) | H (%) | N (%) |
|---|---|---|---|
| Found | 62.71 | 8.96 | 8.37 |
| Calculated | 63.13 | 8.97 | 8.50 |

EXAMPLE 5

N,N,N',N'-tetrakis(2,2,6,6-tetramethyl-4-piperidinyloxycarbonylmethyl)isophthalamide (HA-5)

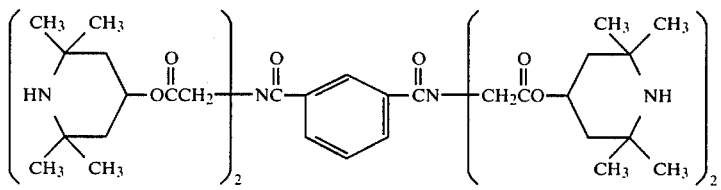

Procedure was carried out in the same manner as in Example 4 except that N,N,N',N'-tetrakis(ethoxycarbonylmethyl)isophthalamide was used in place of N,N,N',N'-tetrakis(ethoxycarbonylmethyl)terephthalamide, to obtain 30.1 g of N,N,N',N'-tetrakis(2,2,6,6-tetramethyl-4-piperidinyloxycarbonylmethyl)isophthalamide as a white crystal (yield, 81%). Melting point, 138°-139° C.

A parent ion peak (952) was confirmed by FD-MS.

| Elementary analysis (for C₅₂H₈₄N₆O₁₀·2H₂O): | | | |
|---|---|---|---|
| | C (%) | H (%) | N (%) |
| Found | 63.66 | 8.73 | 8.42 |
| Calculated | 63.13 | 8.97 | 8.50 |

EXAMPLE 6

N,N-bis(2,2,6,6-tetramethyl-4-piperidinyloxycarbonylmethyl)cyclohexanecarboxylic acid amide (HA-6)

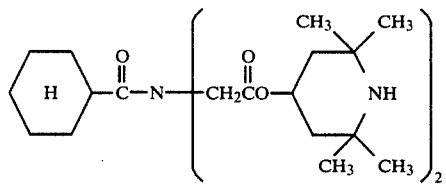

To the same reactor as in Example 1 were added 24.0 g (0.080 mole) of N,N-bis(ethoxycarbonylmethyl)cyclohexanecarboxylic acid amide, 27.7 g (0.176 mole) of 2,2,6,6-tetramethyl-4-piperidinol, 50 ml of toluene and 1.0 g (0.009 mole) of potassium tert-butoxide, and reaction was carried out at 110° to 130° C. for 8 hours, during which the solvent was distilled.

After completion of the reaction, the reaction mixture was cooled to room temperature and dissolved in 50 ml of toluene. The catalyst was removed by filtration, and the filtrate was treated with activated charcoal. Toluene in the filtrate was removed by evaporation, and the residue obtained was recrystallized from n-hexane to obtain 28.4 g of N,N-bis(2,2,6,6-tetramethyl-4-piperidinyloxycarbonylmethyl)cyclohexanecarboxylic acid amide as a white crystal (yield, 68%). Melting point, 124°-126° C.

A parent ion peak (521) was confirmed by FD-MS.

| Elementary analysis (for C₂₉H₅₁N₃O₅): | | | |
|---|---|---|---|
| | C (%) | H (%) | N (%) |
| Found | 66.47 | 9.98 | 8.00 |
| Calculated | 66.76 | 9.85 | 8.05 |

EXAMPLE 7

N,N-bis(2,2,6,6-tetramethyl-4-piperidinyloxycarbonylmethyl)dodecanecarboxylic acid amide (HA-7)

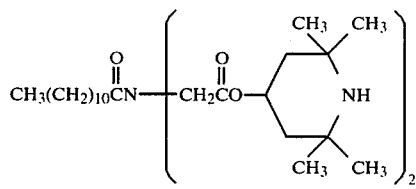

To a 300-ml flask equipped with a thermometer, a dropping funnel and a stirrer were added 37.0 g (0.090 mole) of bis(2,2,6,6-tetramethyl-4-piperidinyl)iminodiacetate, 10.0 g (0.099 mole) of triethylamine and 100 ml of toluene, and 19.7 g (0.090 mole) of lauroyl chloride was added dropwise over 1 hour from the dropping funnel. After dropwise addition, stirring was continued for 30 minutes. The reaction mass was washed with two 50-ml portions of water, and toluene in the organic layer was removed by distillation. The residue obtained was recrystallized from hexane to obtain 46.0 g of N,N-bis(2,2,6,6-tetramethyl-4-piperidinyloxycarbonylmethyl)dodecanecarboxylic acid amide as a white crystal (yield, 86%). Melting point, 73°-74° C.

A parent ion +1 peak (594) was confirmed by FD-MS.

| Elementary analysis (for C₃₄H₆₃N₃O₅): | | | |
|---|---|---|---|
| | C (%) | H (%) | N (%) |
| Found | 68.38 | 10.63 | 7.07 |
| Calculated | 68.76 | 10.69 | 7.08 |

EXAMPLE 8

N,N-bis(2,2,6,6-tetramethyl-4-piperidinyloxycarbonylmethyl)benzamide (HA-8)

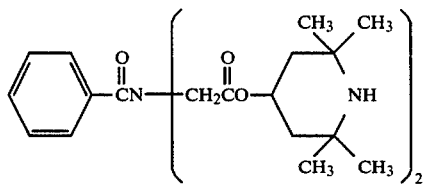

Reaction and after-treatment were carried out in the same manner as in Example 7 except that 12.6 g (0.090 mole) of benzoyl chloride was used in place of 19.7 g (0.090 mole) of lauroyl chloride, to obtain 40.8 g of N,N-bis(2,2,6,6-tetramethyl-4-piperidinyloxycarbonylmethyl)benzamide as a white crystal (yield, 88%). Melting point, 103°-106° C.

A parent ion +1 peak (516) was confirmed by FD-MS.

| Elementary analysis (for $C_{29}H_{45}N_3O_5$): | | | |
|---|---|---|---|
| | C (%) | H (%) | N (%) |
| Found | 67.19 | 8.79 | 8.11 |
| Calculated | 67.54 | 8.80 | 8.15 |

EXAMPLE 9

N,N-bis(1,2,2,6,6-pentamethyl-4-piperidinyloxycarbonylmethyl)cyclohexanepropionamide (HA-9)

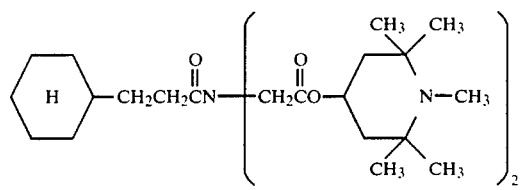

To the same reactor as in Example 7 were added 39.6 g (0.090 mole) of bis(1,2,2,6,6-pentamethyl-4-piperidinyl)iminodiacetate, 10.0 g (0.099 mole) of triethylamine and 200 ml of n-heptane, and after the temperature was raised to 60° C., 15.7 g (0.090 mole) of cyclohexanepropionyl chloride was added dropwise over 1 hour from the dropping funnel. After dropwise addition, stirring was continued for 30 minutes. The reaction mass was washed with 50 ml of water, and n-heptane in the organic layer was distilled. The residue obtained was purified by chromatography to obtain 13.0 g of N,N-bis(1,2,2,6,6-pentamethyl-4-piperidinyloxycarbonylmethyl)cyclohexanepropionamide as a pale yellow, transparent and viscous product (yield, 25%).

A parent ion peak (577) was confirmed by FD-MS.

| Elementary analysis (for $C_{33}H_{59}N_3O_5$): | | | |
|---|---|---|---|
| | C (%) | H (%) | N (%) |
| Found | 68.90 | 10.30 | 7.40 |
| Calculated | 68.59 | 10.29 | 7.27 |

EXAMPLE 10

N,N,N',N'-tetrakis(1,2,2,6,6-pentamethyl-4-piperidinyloxycarbonylmethyl)-1,4-cyclohexanedicarboxylic acid amide (HA-10)

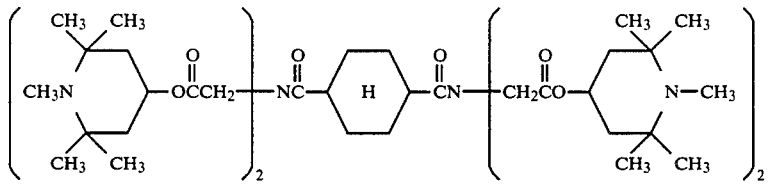

To the same reactor as in Example 7 were added 44.0 g (0.100 mole) of bis(1,2,2,6,6-pentamethyl-4-piperidinyl)iminodiacetate, 10.6 g (0.105 mole) of triethylamine and 100 ml of butyl acetate, and after the temperature was raised to 60° C., 10.5 g (0.050 mole) of 1.4-cyclohexanedicarboxylic acid chloride was added dropwise over 1 hour. After completion of dropwise addition, after-treatment and purification were carried out in the same manner as in Example 9 to obtain 11.7 g of N,N,N',N'-tetrakis(1,2,2,6,6-pentamethyl-4-piperidinyloxycarbonylmethyl)-1,4-cyclohexanedicarboxylic acid amide as a pale yellow viscous product (yield, 22%).

A parent ion peak (1014) was confirmed by FD-MS.

| Elementary analysis (for $C_{56}H_{98}N_6O_{10}$): | | | |
|---|---|---|---|
| | C (%) | H (%) | N (%) |
| Found | 66.10 | 9.92 | 8.27 |
| Calculated | 66.24 | 9.73 | 8.28 |

EXAMPLE 11

N,N-bis(1,2,2,6,6-pentamethyl-4-piperidinyloxycarbonyl-1-methylethyl)cyclohexanepropionamide (HA-11)

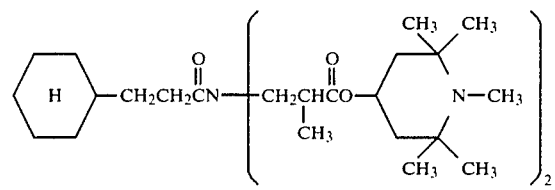

To the same reactor as in Example 7 were added 44.6 g (0.090 mole) of bis(1,2,2,6,6-pentamethyl-4-piperidinyl)iminobis(2-methylpropionate) and 200 ml of toluene, and 15.7 g (0.090 mole) of cyclohexanepropionyl chloride was added dropwise over 1 hour from the dropping funnel. After dropwise addition, stirring was continued for 30 minutes. The reaction mass was washed with 50 g (0.047 mole) of 10% aqueous sodium carbonate and then with 50 ml of water, and toluene in the organic layer was distilled. The residue obtained was purified by chromatography to obtain 5.8 g of a yellow and viscous N,N-bis(1,2,2,6,6-pentamethyl-4-piperidinyloxycarbonyl-1-methylethyl)cyclohexanepropionamide (yield, 10.2%).

A parent ion peak (633) was confirmed by FD-MS.

| Elementary analysis (for $C_{37}H_{67}N_3O_5$): | | | |
|---|---|---|---|
| | C (%) | H (%) | N (%) |
| Found | 69.54 | 11.18 | 6.45 |
| Calculated | 70.10 | 10.65 | 6.63 |

EXAMPLE 12

The blend described below was mixed on a mixer for 5 minutes and then melt-kneaded at 180° C. on a mixing roll to obtain a compound. This compound was formed into a sheet of 1 mm in thickness on a hot press kept at 210° C., and test pieces of 150×30×1 mm (thick) were prepared therefrom.

The test piece thus obtained was exposed to light in a Sunshine weather meter (light source, carbon arc; temperature of black panel, 83°±3° C.; spraying cycle, 120 minutes; and spraying time, 18 minutes) and bent like lobster every 60 hours to obtain a time required for the test piece to break into two. The weathering resistance was evaluated by this time.

| Compounding: | |
|---|---|
| Unstabilized polypropylene | 100 parts by weight |
| Calcium stearate | 0.1 parts by weight |
| Test compound | 0.15 parts by weight |

The result is shown in Table 2.

In the table, UVA-1 to UVA-3 are as shown in Table 1, and HA-1 to HA-11 are compounds obtained in Examples 1 to 11, respectively.

TABLE 1

| UVA-1 | 2-(2-Hydroxy-3-tert-butyl-5-methylphenyl)-5-chlorobenzotriazole |
|---|---|
| UVA-2 | Bis(2,2,6,6-tetramethyl-4-piperidinyl) sebacate |
| UVA-3 | 4-Benzoyloxy-2,2,6,6-tetramethylpiperidine |

TABLE 2

| Example | No. | Light stabilizer | Light fastness (hr) |
|---|---|---|---|
| Present example | 1 | HA-1 | 1140 |
| | 2 | HA-2 | 1080 |
| | 3 | HA-3 | 1140 |
| | 4 | HA-4 | 1260 |
| | 5 | HA-5 | 1200 |
| | 6 | HA-6 | 1080 |
| | 7 | HA-7 | 1140 |
| | 8 | HA-8 | 1080 |
| | 9 | HA-9 | 1140 |
| | 10 | HA-10 | 1200 |
| | 11 | HA-11 | 1030 |
| Comparative example | 12 | UVA-1 | 360 |
| | 13 | UVA-2 | 960 |
| | 14 | UVA-3 | 840 |
| | 15 | No addition | 120 |

EXAMPLE 13

The ingredients mentioned below were blended on a mixer for 5 minutes and then melt-kneaded at 180° C. on a mixing roll to obtain a compound. This compound was formed into a sheet of 1 mm in thickness on a hot press of 210° C., and test pieces of 150×30×1 mm were prepared therefrom.

The test piece thus prepared was exposed to light in a sunshine weather meter (light source, carbon arc; temperature of black panel 83±3° C.; spraying cycle 120 minutes; spraying time 18 minutes), and bent like lobster every 60 hours to measure the time required for the test piece to break into two. The weathering resistance was evaluated by this time. The results are shown in Table 3.

| Compounding: | |
|---|---|
| Unstabilized polypropylene | 100 parts by weight |
| Calcium stearate | 0.1 parts by weight |
| 2,6-di-t-butyl-4-methylphenol | 0.05 parts by weight |
| Test compound: | |
| Light stabilizer | 0.2 parts by weight |
| Phenolic compound | 0.05 parts by weight |
| Sulfur-containing compound | 0.25 parts by weight |

In the table AO-1 to AO-3 indicated in Table 3 are the following compounds:

AO-1: Tris(3,5-di-t-butyl-4-hydroxybenzyl)isocyanurate
AO-2: Dilauryl-3,3'-thiodipropionate
AO-3: Pentaerythritol tetrakis(3-dodecylthiopropionate)

TABLE 3

| No. | Light stabilizer | Phenolic compound | Sulfur-containing compound | Light fastness (hrs.) | Thermal embrittlement induction period (hrs.) |
|---|---|---|---|---|---|
| Present example | | | | | |
| 1 | HA-1 | AO-1 | AO-2 | 1740 | 690 |
| 2 | HA-2 | " | " | 1680 | 670 |
| 3 | HA-3 | " | " | 1740 | 690 |
| 4 | HA-4 | " | " | 1860 | 720 |
| 5 | HA-5 | " | " | 1800 | 710 |
| 6 | HA-6 | " | " | 1680 | 670 |
| 7 | HA-7 | " | " | 1740 | 690 |
| 8 | HA-8 | " | " | 1680 | 680 |
| 9 | HA-9 | " | " | 1740 | 690 |
| 10 | HA-10 | " | " | 1800 | 700 |
| 11 | HA-11 | " | " | 1680 | 670 |
| 12 | HA-1 | " | AO-3 | 1740 | 670 |
| 13 | HA-2 | " | " | 1680 | 650 |
| 14 | HA-3 | " | " | 1740 | 670 |
| 15 | HA-4 | " | " | 1860 | 690 |
| Comparative example | | | | | |
| 16 | UVA-1 | " | AO-2 | 720 | 500 |
| 17 | UVA-2 | " | " | 960 | 485 |
| 18 | UVA-3 | " | " | 900 | 480 |
| 19 | UVA-1 | " | AO-3 | 680 | 480 |
| 20 | UVA-2 | " | " | 900 | 475 |
| 21 | UVA-3 | " | " | 840 | 470 |
| 22 | (not added) | | | 120 | 5 |

What is claimed is:

1. A piperidine compound by the formula (I),

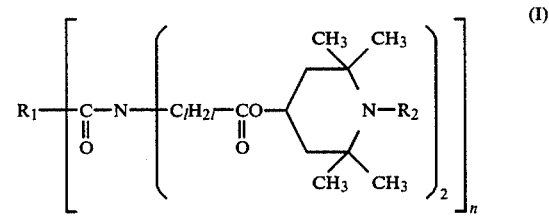

wherein $R_1$ is a uni- or divalent carboxylic acid residue, $R_2$ is a hydrogen atom or a $C_1-C_3$ alkyl or $C_1-C_{18}$ alkyl carbonyl group, l is an integer of 1 to 3 and n is 1 or 2, said univalent carboxylic acid residue being selected from the group consisting of (a) univalent carboxylic acid residues wherein the carboxylic acid residue is a $C_1-C_{20}$ alkyl group, (b) univalent carboxylic acid residues having a cyclohexyl group linked to the end of the carboxylic acid residue of (a), and (c) univalent carboxylic acid residues having a phenyl group linked to the end of the carboxylic acid residue of (a), said divalent carboxylic acid residue being selected from the group consisting of (d) divalent carboxylic acid residues wherein the carboxylic acid residue is a $C_1-C_{18}$ alkyl group, (e) divalent carboxylic acid residues wherein the carboxylic acid residue is a single bond, (f) divalent carboxylic acid residues wherein the carboxylic acid residue is a $C_5-C_{16}$ cycloalkyl group, (g) divalent carboxylic acid residues wherein the carboxylic acid residue is an aromatic group having 6 or 10 carbon atoms, (h) divalent carboxylic acid residues wherein the carboxylic acid residue is an alkyl group having a phenyl group linked to the side or main chain, the alkyl moiety having 1 to 16 carbon atoms and (i) $C_4$-$C_{20}$ divalent carboxylic acid residues having a carbon or sulfur atom in the carboxylic acid residue.

2. A method for producing a piperidine compound represented by the formula (I),

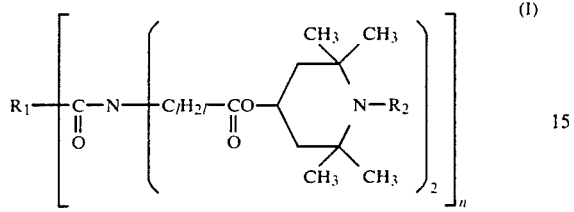

wherein $R_1$ is a uni- or divalent carboxylic acid residue, $R_2$ is a hydrogen atom or a $C_1$-$C_3$ alkyl or $C_1$-$C_{18}$ alkyl carbonyl group, l is an integer of 1 to 3 and n is 1 or 2, characterized in that an iminodialkanoic acid compound represented by the formula (II),

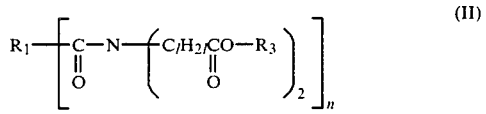

wherein $R_1$, l and n have the same meanings as described in claim 1, and $R_3$ is a $C_1$-$C_4$ alkyl group, is reacted with a piperidinol compound represented by the formula (III),

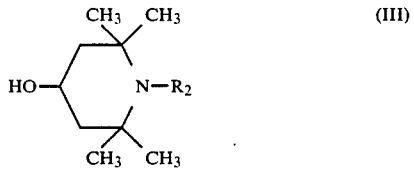

wherein $R_2$ has the same meaning as described in claim 1.

3. A method as claimed in claim 2 wherein the reaction is carried out in the presence of a solvent selected from the group consisting of aromatic hydrocarbons, aliphatic hydrocarbons, alicyclic hydrocarbons, water-soluble polar solvents, ethers and alcohols.

4. A method as claimed in claim 2 wherein the reaction is carried out in the presence of a basic catalyst.

5. A method as claimed in claim 4 wherein the basic catalyst is selected from the group consisting of metal hydroxides, metal hydrides, metal amides, alkali metal alkoxides and alkali metal phenoxides.

6. A method as claimed in claim 2 wherein the reaction is carried out at a temperature in the range of 0° to 200° C.

7. A method as claimed in claim 2 wherein the molar ratio of the piperidinol compound of the formula (III) to the iminodialkanoic acid derivative of the formula (II) is in the range of 2:1 to 5:1 when n is 1, and 4:1 to 10:1 when n is 2.

8. A method for producing a piperidine compound represented by the formula (I)

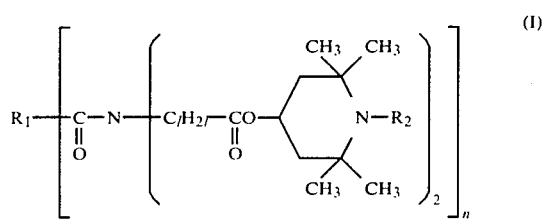

wherein $R_1$ is a uni- or divalent carboxylic acid residue, $R_2$ is a hydrogen atom or a $C_1$-$C_3$ alkyl or $C_1$-$C_{18}$ alkyl carbonyl group, l is an integer of 1 to 3 and n is 1 or 2, characterized in that an iminodialkanoic acid compound represented by the formula (IV),

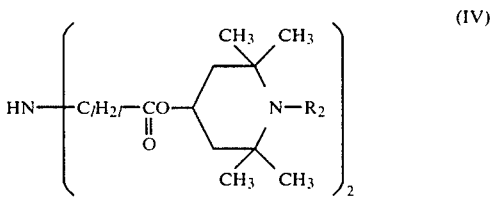

wherein $R_2$ and l have the same meanings as described in claim 1, is reacted with a carboxylic acid halide represented by the formula (V),

wherein $R_1$ and n have the same meanings as described in claim 1, and X is a halogen atom.

9. A method as claimed in claim 8 wherein the reaction is carried out in an inert solvent in the presence of a dehydrohalogenating agent.

10. A method as claimed in claim 9 wherein the inert solvent is selected from the group consisting of aliphatic hydrocarbons, alicyclic hydrocarbons, aromatic hydrocarbons, water-soluble polar solvents, ethers, halogenated hydrocarbons and esters.

11. A method as claimed in claim 8 wherein the molar ratio of the iminodialkanoic acid compound of the formula (IV) to the uni- or divalent carboxylic acid halide of the formula (V) is in the range of 0.9:1 to 1.1:1 for the univalent carboxylic acid halide and 1.8:1 to 2.2:1 for the divalent carboxylic acid halide.

12. A method as claimed in claim 8 wherein the reaction is conducted at a temperature in the range of −30° to 120° C.

13. A stabilizer for organic substances containing a piperidine compound represented by the formula (I),

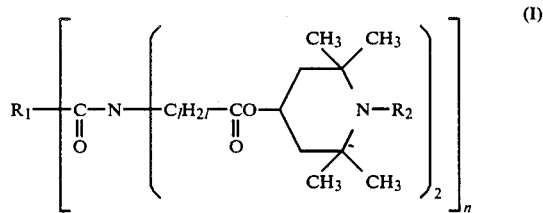

wherein $R_1$ is a uni- or divalent carboxylic acid residue, $R_2$ is a hydrogen atom or a $C_1$–$C_3$ alkyl or $C_1$–$C_{18}$ alkyl carbonyl group, l is an integer of 1 to 3 and n is 1 or 2, as an effective ingredient, said univalent carboxylic acid residue being selected from the group consisting of (a) univalent carboxylic acid residues wherein the carboxylic acid residue is a $C_1$–$C_{20}$ alkyl group, (b) univalent carboxylic acid residues having a cyclohexyl group linked to the end of the carboxylic acid residue of (a), and (c) univalent carboxylic acid residues having a phenyl group linked to the end of the carboxylic acid residue of (a), said divalent carboxylic acid residue being selected from the group consisting of (d) divalent carboxylic acid residues wherein the carboxylic acid residue is a $C_1$–$C_{18}$ alkyl group, (e) divalent carboxylic acid residues wherein the carboxylic acid residue is a single bond, (f) divalent carboxylic acid residues wherein the carboxylic acid residue is a $C_5$–$C_{16}$ cycloalkyl group, (g) divalent carboxylic acid residues wherein the carboxylic acid residue is an aromatic group having 6 or 10 carbon atoms, (h) divalent carboxylic acid residues wherein the carboxylic acid residue is an alkyl group having a phenyl group linked to the side or main chain, the alkyl moiety having 1 to 16 carbon atoms and (i) $C_4$–$C_{20}$ divalent carboxylic acid residues having a carbon or sulfur atom in the carboxylic acid residue.

14. A stabilizer as claimed in claim 13 which further contains a phosphite type antioxidant.

15. A stabilizer as claimed in claim 14 wherein the phosphite type antioxidant is selected from the group consisting of tris(nonylphenyl)phosphite, distearyl pentaerythritol diphosphite, tris(2,4-di-tert-butylphenyl)phosphite, tris(2-tert-butyl-4-methylphenyl)phosphite, bis(2,4-di-tert-butylphenyl)pentaerythritol diphosphite and tetrakis(2,4-di-tert-butylphenyl)4,4'-biphenylene diphosphite.

16. A stabilizer as claimed in claim 13 which further contains a sulfur-containing antioxidant.

17. A stabilizer as claimed in claim 16 wherein the sulfur-containing antioxidant is selected from the group consisting of dilauryl thiodipropionate, dimyristyl thiodipropionate, distearyl thiodipropionate, pentaerythritol tetrakis($\beta$-laurylthiopropionate) and pentaerythritol tetrakis($\beta$-hexylthiopropionate).

18. A stabilized organic material stabilized by the stabilizer according to any of claims 13.

19. A stabilized organic material stabilized by the stabilizer according to any of claims 14 to 17.

20. A stabilized organic material as claimed in claim 18 or 19 wherein the organic material stabilized is a synthetic resin selected from low-density polyethylene, high-density polyethylene, linear low-density polyethylene, chlorinated polyethylene, EVA resin, polypropylene, polyvinyl chloride, methacrylic resin, polystyrene, impact-resistant polystyrene, ABS resin, AES resin, MBS resin, polyethylene terephthalate, polybutylene terephthalate, polyamide, polyimide, polycarbonate, polyacetal, polyurethane, and unsaturated polyester resin.

21. A stabilized organic material as claimed in claim 18 or 19 wherein the organic material stabilized is selected from oil paints, spirit paints, cellulose derivative paints, synthetic resin paints, synthetic resin emulsion paints and water-based baking paints.

22. A stabilized organic material as claimed in claim 18 wherein the amount of the stabilizer is 0.01 to 5 parts by weight based on 100 parts by weight of the organic material.

* * * * *